(12) United States Patent
Zhang et al.

(10) Patent No.: US 11,452,473 B2
(45) Date of Patent: Sep. 27, 2022

(54) MEDICAL DEVICE WITH CAPACITIVE SENSING FUNCTION

(71) Applicant: Johnson Electric International AG, Murten (CH)

(72) Inventors: Libing Zhang, Sharon, MA (US); Anil Babu, Miamisburg, OH (US); Kenneth Heberling, Royal Oak, MI (US); Joseph Mello, Tipp City, OH (US); Timothy Carney, Vandalia, OH (US); Hanna Alesi, Lebanon, OH (US)

(73) Assignee: JOHNSON MEDTECH LLC, Vandalia, OH (US)

( * ) Notice: Subject to any disclaimer, the term of this patent is extended or adjusted under 35 U.S.C. 154(b) by 652 days.

(21) Appl. No.: 16/274,215

(22) Filed: Feb. 12, 2019

(65) Prior Publication Data

US 2020/0253525 A1 Aug. 13, 2020

(51) Int. Cl.
*A61B 5/15* (2006.01)
*A61B 5/0531* (2021.01)
(Continued)

(52) U.S. Cl.
CPC ...... *A61B 5/150801* (2013.01); *A61B 5/0531* (2013.01); *A61B 5/150267* (2013.01);
(Continued)

(58) Field of Classification Search
CPC ............. A61M 5/002; A61M 5/14244; A61M 5/14248; A61M 5/172; A61M 5/20; A61M 5/31; A61M 5/3202; A61M 5/5086; A61M 2005/14252; A61M 2005/14256; A61M 2005/1426; A61M 2005/14272; A61M 2005/2006; A61M 2005/206; A61M 2005/3022; A61M 15/0043; A61M 25/002; A61M 2205/13; A61M 2205/14; A61M 2205/15; A61M 2205/3317; A61M 2205/58; A61M 2209/06; A61B 5/0531;
(Continued)

(56) References Cited

U.S. PATENT DOCUMENTS 9,427,529 B2 * 8/2016 Cabiri ................. A61M 5/3287
2009/0076336 A1 * 3/2009 Mazar .................... A61B 5/318
600/300
(Continued)

FOREIGN PATENT DOCUMENTS

| EP | 3348284 A2 | 7/2018 |
|---|---|---|
| WO | 2006067217 A2 | 6/2006 |
| WO | 2010/029054 A1 | 3/2010 |

*Primary Examiner* — Kami A Bosworth
(74) *Attorney, Agent, or Firm* — Aird & McBurney LP

(57) ABSTRACT

A medical device with a capacitive sensing function includes a medical body having a syringe and a sensing circuit having an electrode, a protective film adhered to the medical body and including a plastic film, an electrode provided on the plastic film and opposite from the electrode of the medical body, and a capacitive sensor formed by the electrode of the medical body and the electrode of the protective film and being a part of the sensing circuit, wherein a capacitance value of the capacitive sensor changed under the condition of removing the protective film from the medical body, the sensing circuit being configured to detect the capacitance value and trigger corresponding function of the medical body.

11 Claims, 4 Drawing Sheets

(51) Int. Cl.
*A61M 5/172* (2006.01)
*G01D 5/24* (2006.01)
*H05K 1/11* (2006.01)

(52) U.S. Cl.
CPC ........... *A61M 5/172* (2013.01); *G01D 5/2405* (2013.01); *H05K 1/11* (2013.01); *H05K 1/111* (2013.01); *H05K 2201/093* (2013.01); *H05K 2201/10053* (2013.01); *H05K 2201/10151* (2013.01)

(58) Field of Classification Search
CPC ........ A61B 5/150267; A61B 5/150717; A61B 5/150725; A61B 5/150801; A61B 5/150961; A61B 5/150969; A61B 5/6833; A61B 5/68335; A61B 50/30; A61B 50/33; B65D 77/2032; G01D 5/2405; H05K 1/11; H05K 1/111; H05K 2201/093; H05K 2201/10053; H05K 2201/10151
See application file for complete search history.

(56) References Cited

U.S. PATENT DOCUMENTS

| | | | | |
|---|---|---|---|---|
| 2012/0215163 | A1* | 8/2012 | Hanson | G01B 7/14 604/67 |
| 2012/0217184 | A1* | 8/2012 | Edwards | A61M 11/00 206/571 |
| 2018/0014787 | A1 | 1/2018 | Ganton | |
| 2018/0306603 | A1* | 10/2018 | Ballam | G01R 27/2605 |
| 2020/0024047 | A1* | 1/2020 | McNannay | H05K 1/0269 |
| 2020/0405951 | A1* | 12/2020 | Barren | A61M 5/3134 |
| 2020/0405952 | A1* | 12/2020 | Rytz | A61M 5/46 |

* cited by examiner

MEDICAL DEVICE WITH CAPACITIVE SENSING FUNCTION

FIELD

The present disclosure relates to a medical device, and more particularly to a medical device including a protective film with capacitive sensors.

BACKGROUND

A patch-like syringe is a medical device that is worn to a specific part of patient when used. The patch-like syringe includes a bottom layer which is attached to a patient's skin by a film, and a needle extending from the bottom layer of the syringe to inject drugs into the patient's body. In general, the syringe further provides a button. After the protective film is removed, the button is manually pressed to activate the syringe to identify whether the syringe has been attached to a patient's skin. If the syringe has been attached to the patient's skin, the syringe automatically pushes the needle out of the housing to puncture the patient's skin and inject drugs into the patient's body, thereby completing an injection process.

This wearable syringe, which provides the mechanical buttons for activating the injection function, reduces manual operation compared with conventional syringes that require manual operation. However, after removing the film, the manual button not only increases the cost, but also increases weight and complexity. Users may also forget to press the button to start the injection after wearing the syringe, which will cause some inconvenience.

Therefore, it is necessary to provide a medical device with capacitive sensing function for solving these and/or other issues.

SUMMARY OF THE DISCLOSURE

In view of this, the present disclosure is designed to provide a medical device with capacitive sensing element which can be automatically driven on condition that a protective film is removed.

A medical device with a capacitive sensing element comprises a medical body including a syringe, a sensing circuit having an electrode, and a protective film adhered to the medical body. The protective film includes a plastic film, and an electrode provided on the plastic film and opposite from the electrode of the medical body. A capacitive sensor is formed by the electrode of the medical body and the electrode of the protective film and configured to be a part of the sensing circuit. A capacitance value of the capacitive sensor is changed on the condition of tearing off the protective film, and the sensing circuit is configured to detect the capacitance value and trigger a corresponding function of the medical body.

In another aspect, the medical body includes a printed circuit board, wherein the electrode of the medical body is provided on the printed circuit board, and wherein the capacitive sensor is formed by the electrode of the printed circuit board and the electrode of the protective film.

In another aspect, the medical body further includes an adhesive layer, and the protective film is adhered to the printed circuit board by the adhesive layer.

In another aspect, the printed circuit board includes a substrate, a ground layer disposed on one side of the substrate, and a signal layer disposed on the other side of substrate and facing the protective film, wherein the electrode of the medical body is provided on the signal layer.

In another aspect, the electrode of the printed circuit board includes a first electrode and a second electrode separated from each other, wherein the electrode of the protective film includes a third electrode and a fourth electrode separated from each other, and wherein the capacitive sensor includes a first capacitive sensor formed by the first electrode together with the third capacitive sensor, and a second capacitive sensor formed by the second electrode together with the fourth capacitive sensor.

In another aspect, the electrode of the protective film is a printed electrode which is made by a conductive ink printing process.

In another aspect, the protective film further includes an insulating strip covering the electrode of the protective film.

In another aspect, a capacitive sensor is formed by the electrode of the printed circuit board in cooperation with an external dielectric on the condition of removing the protective film.

In another aspect, a contact pad is disposed on the ground layer, the medical body further includes a switch having a contact which is configured to electrically connect the contact pad for triggering the sensing of a wearable sensing circuit.

In another aspect, the contact pad includes a first pad, a second pad, and a third pad aligned in a row, and the second pad and the third pad are electrically connected with the corresponding two electrodes of the printed circuit board by two conductive traces, respectively.

In another aspect, the patch type medical device is a patch type injection device, a patch type blood drawing device or a patch type needle pulling device.

In the patch type medical device of the present disclosure, an electrode is disposed on the protective film, and the capacitance value of a sensing circuit is changed by tearing off the protective film, thereby triggering a corresponding function. Compared with a traditional scheme, which uses buttons to trigger corresponding functions, it simplifies the design and cost of medical devices, reduces the weight of medical devices and is more user-friendly.

BRIEF DESCRIPTION OF THE DRAWINGS

Many aspects of the embodiments can be better understood with reference to the following drawings. The components in the drawings are not necessarily drawn to scale, the emphasis instead being placed upon clearly illustrating the principles of the embodiment.

DETAILED DESCRIPTION OF THE PREFERRED EMBODIMENTS

Figure 1:
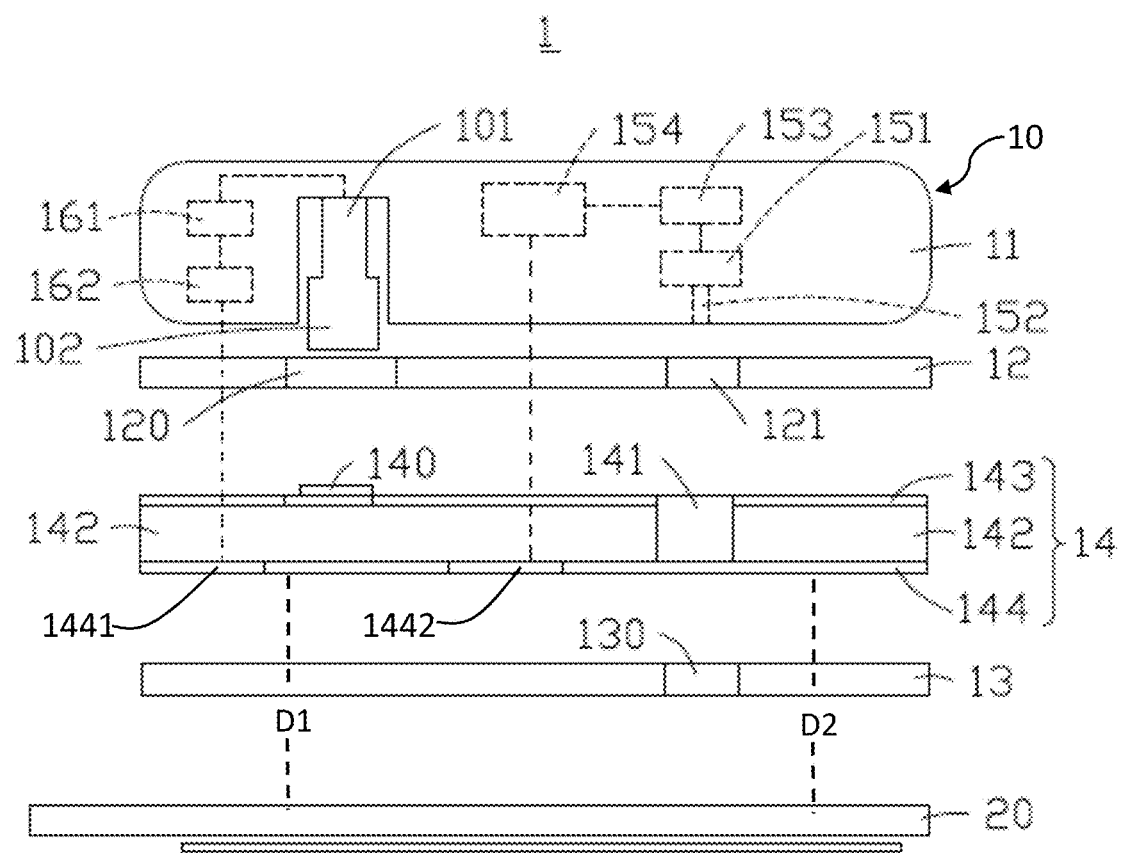
FIG. 1 is a schematic cross-sectional view of a medical device with a capacitive sensing function in accordance with an exemplary embodiment of the present disclosure.

Embodiments of the present disclosure will be described in detail in conjunction with the drawings. It should be noted that the figures are illustrative rather than limiting. The figures are not drawn to scale, do not illustrate every aspect of the described embodiments, and do not limit the scope of the present disclosure.

It should be noted that when a component is considered to be "connected" to another component, it can be directly connected to another component or a central component can be present between two components at the same time. When a component is considered to be "provided with" another component, it may be arranged directly on another component or possibly with a centered component.

Unless otherwise defined, all technical and scientific terms used herein have the same meaning, which is used in the description of the present disclosure to describe specific embodiments and is not intended to limit the disclosure. The term "or/and" used here includes any and all combinations of one or more of the associated listed items.

The present disclosure provides a patch-type medical device capable of detecting whether a protective film is torn off and activating a corresponding function after removing the protective film.

Specifically, the present disclosure provides a patch-type medical device including a medical body, a protective film bonded to the medical body and having at least one electrode, and the medical body including at least one sensing circuit. A capacitor unit is accordingly formed by the electrode cooperatively with an electrode region of the medical body, and the capacitor unit as a part of the sensing circuit. The value of the capacitor unit changes after the protective film is removed, and the sensing circuit detects the changed capacitance value and triggers the medical body to perform a corresponding function, such as an automated electrical connection instead of being manually pressed by a user to effect an electrical connection. When the electrode region of the medical body is kept in contact with an external dielectric such as human skin, the electrode region and an external medium may be electrically coupled, causing a change in the capacitance value, thereby activating the medical body to activate the corresponding function.

More specifically, the medical body includes a printed circuit board with an electrode, and the sensing circuit is designed on the printed circuit board. The electrode disposed on the protective film and the electrode region on the printed circuit board forms a capacitive sensor. While the protective film is removed, a capacitance value of the capacitive sensor is detected by the sensing circuit, which may be indicative that the protective film is detached from the medical body and a corresponding sensing may be triggered. A wearable sensing circuit further detects whether the medical body is pasted on a patient's skin. The electrode region on the circuit board is another conductive electrode in this embodiment.

After the protective film is removed, the sensing electrode of the PCB is in contact with a target object such as a patient's skin to form another capacitive sensor, and in the event that the capacitance value of the sensing electrode changes, it will trigger the medical body to perform corresponding functions, such as injection, blood drawing, etc.

The following examples are illustrated with an embodiment of a capacitive sensing medical device.

Referring to FIG. 1, a medical device 1 with a capacitive sensing function according to an embodiment of the present disclosure includes a medical body 10 having a housing 11, a protective film 20 adhered to the medical body 10, two adhesive layers 12, 13 and a printed circuit board 14. The housing is not only in the shape of a rectangular patch or a circular patch like this, but also in shape which may be set according to an actual requirement. In general, the protective film 20 is adhered to the medical body 10 by glue or medical adhesive plaster. One side of the printed circuit board 14 is adhered to the housing 11 by a first adhesive layer 12, and another side is adhered to the protective film 20 by a second adhesive layer 13. The printed circuit board 14 is received into the housing 11, and the protective film 20 is exposed outside of the housing 11 of the medical body 10. In this embodiment, the first adhesive layer 12 is an acrylic adhesive layer with a thickness of 50 μm. The second adhesive layer 13 is a medical adhesive layer which may avoid damage of the skin. After the protective film 20 is removed, the medical body 10 is directly adhered to human body by the second adhesive layer 13.

In the embodiment, the medical device 1 further includes a syringe 151 received in the housing 11, a needle 152 coupled to an end of the syringe 151, a first actuator 153 for actuating the syringe 151, and a first controlling unit 154 for controlling the first actuator 153 to actuate the syringe 151. In additional, the medical device 1 further includes a switch 101 received in the medical body 10. The switch 101 includes a contact 102 used for transmitting electrical signal, a second actuator 161 for actuating the contact 102 and a second controlling unit 162 for controlling the second actuator 161 to actuate the elastic contact 102. The second controlling unit 162 sends a signal to the second actuator 161 in proper time so as to drive the contact 102. Furthermore, the printed circuit board 14 includes a sensing circuit 1441 having a contact pad 140 which is electrically connected to the contact 102, and a wearable sensing circuit 1442 configured for detecting whether the medical body 10 is in contact with the patient's skin or other targets. More specifically, when the protective film 20 is removed from the medical body 10, the sensing circuit 1441 detects a change in a capacitance value of the printed circuit board 14, which may activate the second controlling unit 162 to trigger the second actuator 161. Accordingly, the second actuator 161 triggers the switch 101 to drive the contact 102. After the contact 102 is actuated, which may be passed through a hole 120 defined in the first adhesive layer 12 to electrically connected to the contact pad 140, thereby turning on the wearable sensing circuit 1442 to detect whether the medical body 10 is in contact with a target, such as patient's body. While the capacitive sensing medical device 1 is attached on the patient's body, the first controlling unit 154 is triggered. The first controlling unit 154 controls the first actuator 153 to actuate the syringe 151, so that the syringe 151 drives the needle 152 to move downwardly, and sequentially passes through a hole 121 provided on the first adhesive layer 12, a hole 141 corresponding to the hole 121 provided on the printed circuit board 14 and a hole 130 corresponding to the hole 141 provided on the second adhesive layer 13, and then the needle 152 penetrates the patient's skin to finally complete the injection of the drug. In other words, while assembled, the contact 102 passes through the hole 120 of the first adhesive layer 12 and is electrically connected to the contact pad 140, and the needle 152 is driven by the actuator 153 to pass through the hole 121 and the hole 141 of the printed circuit board 14 and the hole 130 to a predetermined position. In one embodiment of the present disclosure, the wearable sensing circuit 1442 detects a change to another capacitance value of the printed circuit board on the condition that the protective film 20 is removed, which triggers the first controlling unit 154. The circuits structures of the sensing circuit 1441 and the wearable sensing circuit 1442 may be obtained in the public know arts, and are not described herein.

Figure 2:
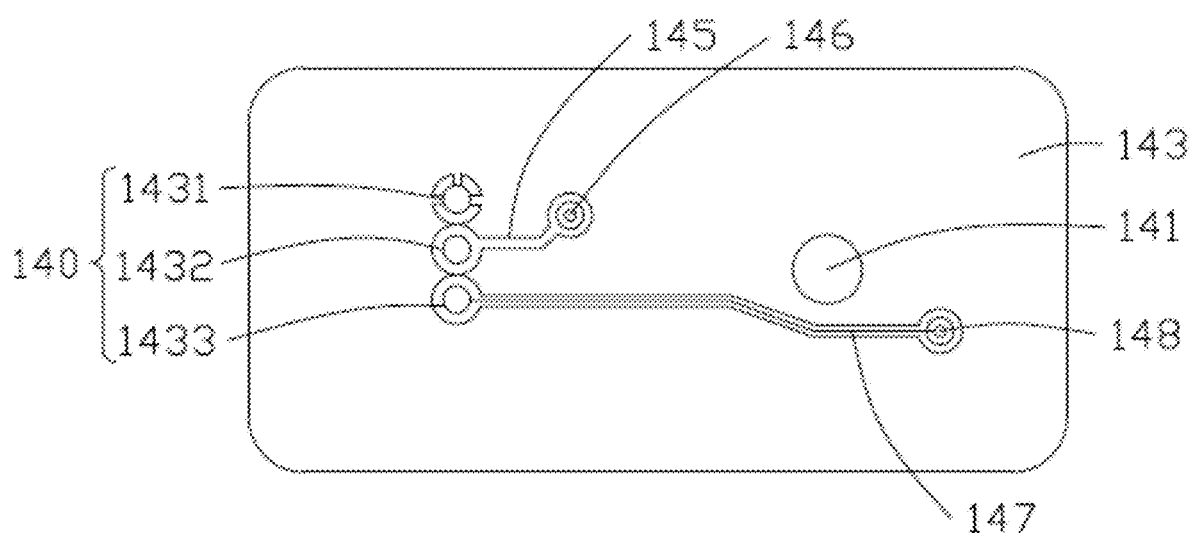
FIG. 2 is a top view of a printed circuit board of the medical device with the capacitive sensing function of FIG. 1.
Figure 3:
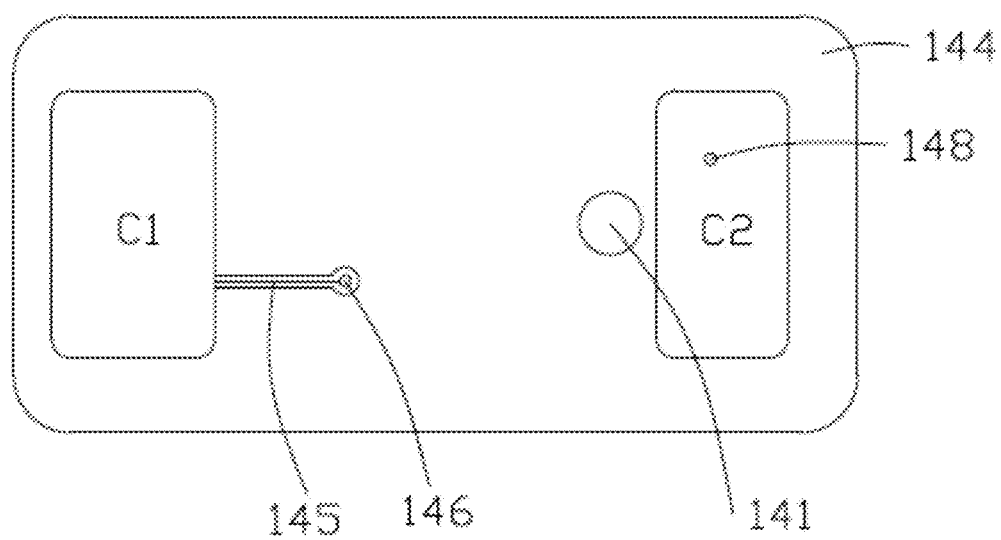
FIG. 3 is a top view of the printed circuit board of FIG. 1, viewed from another viewpoint.
Figure 5:
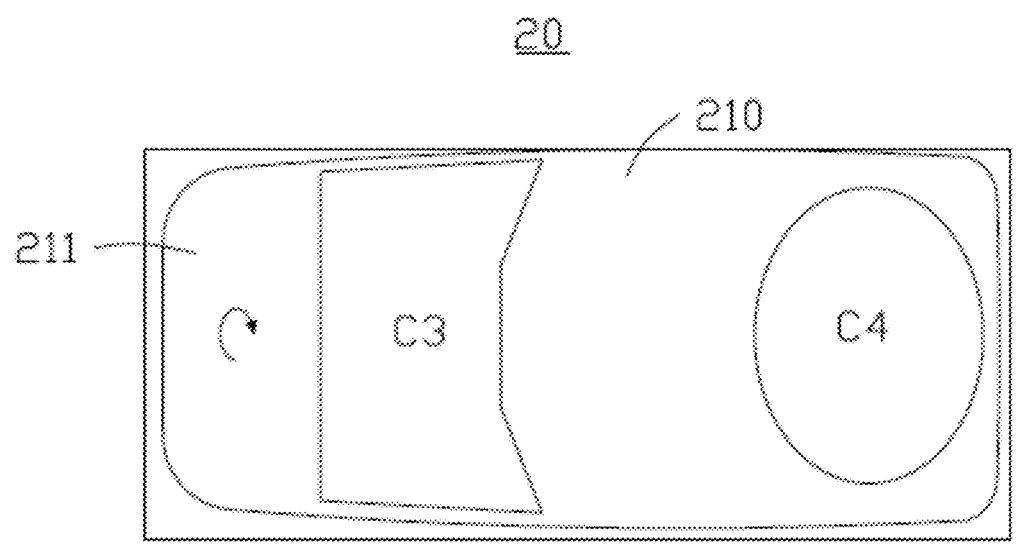
FIG. 5 is a top view of the protective film shown in FIG. 4, with an insulating strip thereof being removed.

In the embodiment, referring to FIGS. 2 and 3, the printed circuit board 14 may be a flexible circuit board and includes a substrate 142 having two sides, a ground layer 143 disposed on one side of the substrate 142 and facing the first adhesive layer 12, and a signal layer 144 disposed on the other side of the substrate 142 and facing the second adhesive layer 13. Optionally, the substrate 142 is usually made of polyethylene terephthalate and has excellent physical and mechanical properties in a wide temperature range. Referring to FIGS. 2, 3 and 5, two electrodes are provided on the signal layer 144. Specifically, a first electrode C1 and a second electrode C2 are separately provided on the signal layer 144 of the printed circuit board 14 and used for being attached to the protective film 20 by the second adhesive layer 13 for forming capacitive sensor. The contact pad 140 disposed on the ground layer 143 includes a first pad 1431, a second pad 1432 and a third pad 1433 aligned in a row. The first pad 1431 is used for grounding to prevent a short circuit. The second pad 1432 is electrically connected to the first electrode C1 via a first conductive trace 145 which passes through a conductive aperture 146 defined on the printed circuit board 14. Similarly, the third pad 1433 is electrically connected to the second electrode C2 via a second conductive trace 147 which passes through another conductive hole 148 defined on the printed circuit board 14. In this embodiment, the sensing circuit 1441 and the wearable sensing circuit 1442 are designed on the signal layer 144, but this is not a unique design. Actually, the position of the sensing circuit 1441 and the wearable sensing circuit 1442 may be set according to the actual requirements, or even designed on another printed circuit board, which may be obtained from any suitable source.

Figure 4:
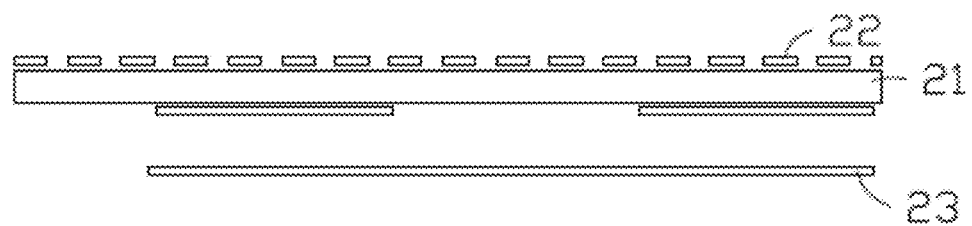
FIG. 4 is an enlarged view of a protective film shown in FIG. 1.

Referring to FIGS. 4 through 5, the protective film 20 not only protects the printed circuit board 14, but also includes some electronic components that may form a capacitive sensor. More specifically, the protective film 20 includes a plastic film 21 made of insulating material, a silicone coating 22 provided on one surface of the plastic film 21 and facing the printed circuit board 14, and a plurality of electrodes disposed on the other surface of the plastic film 21 and far away from the printed circuit board 14. The protective film 20 is easily removed from the medical body 10 via the silicone coating 22. In order to avoid the electrodes from staining and interfering, an insulating strip 23 is provided to cover the surface of a plurality of electrodes provided on the plastic film 21. The plastic film 21 has a main body 210 for protecting the plurality of electrodes of the protective film 20, a thin piece 211 extending from the body 210. The thin piece 211 is easy for a user to grasp and pull to remove the protective film 20 from the medical body 10, thereby exposing the second adhesive layer 13, whereupon the user then sticks the medical body 10 onto the patient's skin by the second adhesive layer 13. In another embodiment, the plurality of electrodes of the protective film 20 are printed electrodes made by a conductive ink printing process.

Furthermore, the plurality of electrodes on the protective film 20 includes a third electrode C3 corresponding to the first electrode C1, and a fourth electrode C4 corresponding to the second electrode C2. The third electrode C3 and the fourth electrode C4 are also separated from each other and have different or the same areas. In the embodiment, an area of the third electrode C3 is greater than that of the first electrode C1 so that a first capacitance value is formed between the first electrode C1 and the third electrode C3, which cooperatively forms a first capacitive sensor D1. An area of the fourth electrode C4 is greater than that of the second electrode C2 so that a second capacitance value is formed between the second electrode C2 and the fourth electrode C4 and is detected by a second capacitive sensor D2 which is electrically connected to a capacitor formed by the fourth electrode C4 and the second electrode C2.

While assembled, the plastic film 21 is sandwiched between the first electrode C1 and the third electrode C3, and between the second electrode C2 and the fourth electrode C4. The first capacitive sensor D1 and the second capacitive sensor D2 are respectively connected to the sensing circuit 1441 via the first electrode C1 and the second electrode C2. The sensing circuit 1441 of capacitive sensing medical device 1 is used to sense whether the capacitance value of the first capacitive sensor D1 has changed, and sense whether the capacitance valve of the second capacitive sensor D2 has changed.

When the protective film 20 is removed from the medical body 10, a distance between the third electrode C3 and the first electrode C1 is enlarged, and a distance between the fourth electrode C4 and the second electrode C2 is also enlarged, which causes a change to the capacitance value of the first capacitive sensor D1 and a change to the capacitance of the second capacitive sensor D2.

The sensing circuit 1441 senses the changes to the capacitance values respectively of the first capacitive sensor D1 and the second capacitive sensor D2 and sends a trigger signal to activate the second controlling unit 162 to control the second actuator 161. The second actuator 161 drives the contact 102 to move downwardly to electrically connect the contact pad 140, thereby making the wearable sending circuit 1442 on a work status.

In the embodiment, only when the protective film 20 has been completely is removed, the first actuator 153 will be triggered by the first controlling unit 154. That is to say, if one of the two electrodes C3 and C4 of the protective film 20 is adhered on the printed circuit board 14, the corresponding capacitance value of the first capacitive sensor D1 or the second capacitive sensor D2 does not change, and as a result the first actuator 153 is not activated. The detecting function of the sensing circuit 1441 is triggered only on the condition that the protective film 20 is completely removed from the medical body 10.

It can be understood that the number of electrodes of the protective film 20 is not limited to one, and more than two electrodes may be disposed on the plastic film 21 of the protective film 20. The number of electrodes on the protective film 20 may be adjusted according to actual requirements, and the number of capacitive sensors is adjusted with the number of electrodes on the protective film 20, which is not limited herein.

It can be understood that a threshold value may be set to reduce misoperation. Only when the change value of the output of the sensing circuit 1441 is greater than a threshold value, the second controlling unit 162 will be triggered to activate the wearable sensing function of the wearable sensing circuit 1442.

It can be understood that, in embodiments in which only one electrode provided on the protective film 20, the area of the electrode may be increased appropriately. For example, the area of the electrode may override the electrodes C3, C4 and the area between the third electrode C3 and the fourth electrode C4. In addition, a threshold may be set to trigger the second controlling unit 162 only when the change in capacitance value is greater than the threshold after the protective film 20 is removed.

In the embodiment, the second adhesive layer 13 not only adheres the protective film 20 to the printed circuit board 14, but also serves as an insulating layer sandwiched between two conductive electrodes. When the protective film 20 is completely removed, the printed circuit board 14 may be attached to a patient's skin such that the first electrode C1 and the second electrode C2 are coupled to the skin to form another capacitive sensor which is configured for outputting an electrical signal to trigger the second controlling unit 162, and as a result the accuracy and sensitivity of the medical body is improved. At this stage, the capacitance value changes from a negative value to a positive value.

As mentioned above, the central idea of the embodiment of the present disclosure is provide an electrode on the protective film 20 so as to form a capacitive sensor, the capacitance value of the capacitance sensor is changed by tearing off the protective film thus triggering the corresponding function of the medical body. Compared with the traditional medical device using the button to trigger the corresponding function, it simplifies the design and cost of medical device and improves the automation and control accuracy of the syringe of the capacitive sensing medical device.

Although the above embodiments are described only with the patch type injection device as an example, the scope of the present disclosure is not limited thereto. The present disclosure may be applied to any medical device which is provided with a sensing electrode on the protective film, which changes the capacitance value of the sensing circuit by tearing off the protective film, thereby triggering the corresponding function of the medical device such as a wearable blood drawing device, a patch type needle device, and the like.

In summary, a medical device provided in the embodiment of the present disclosure has at least one electrode disposed on the protective film for forming a corresponding capacitive sensor, and the capacitance value of the sensing circuit is changed by tearing off the protective film, thereby triggering a corresponding function. When the protective film 20 is removed from the printed circuit board 14, the capacitance value of the capacitive sensor would be changed so as to activate the medical device 1 with a capacitive sensing function to start working. Once a patient's skin is detected, the actuator will drive the syringe 151 automatically. Compared with a traditional scheme, which uses buttons to trigger corresponding functions, it simplifies the design and cost of medical devices, reduces the weight of medical devices and is more user-friendly.

While the present disclosure has been described with reference to a specific embodiment, the description of the disclosure is illustrative and is not to be construed as limiting the disclosure. Various modifications to the present disclosure can be made to the exemplary embodiment by those skilled in the art without departing from the true spirit and scope of the disclosure as defined by the appended claims.

The invention claimed is:

1. A medical device with electrical sensing function comprising:
    a medical body having at least one electrode;
    a protective film adhered to the medical body; and
    wherein the protective film comprises a plastic film, at least one electrode provided on a side of the plastic film away from the medical body, an electrical sensor is formed by said at least one electrode of the medical body cooperating with said at least one electrode of the protective film, the medical device further comprises a sensing circuit responsive to the electrical sensor, wherein the electrical sensor is configured to generate an electrical signal in response to removing the protective film from the medical body, and the sensing circuit is configured to detect the electrical signal and trigger a corresponding function of the medical body;
    wherein the medical body comprises a printed circuit board with a contact pad disposed on the printed circuit board, the medical body further comprises a switch having a contact, the corresponding function of the medical body being a triggering of the switch to urge the contact to be electrically connected to the contact pad, to thereby activate a wearable sensing circuit.

2. The medical device with electrical sensing function as described in claim 1, wherein said at least one electrode of the medical body is provided on the printed circuit board, the electrical sensor is a capacitive sensor, and the electrical signal is a change of a capacitance value of the capacitive sensor.

3. The medical device with electrical sensing function as described in claim 2, wherein the medical body further comprises an adhesive layer, the protective film is adhered to the printed circuit board by the adhesive layer.

4. The medical device with electrical sensing function as described in claim 2, wherein the printed circuit board comprises a substrate, a ground layer disposed on one side of the substrate, a signal layer disposed on another side of the substrate and facing the protective film, said at least one electrode of the medical body is provided on the signal layer.

5. The medical device with electrical sensing function as described in claim 4, wherein the at least one electrode of said printed circuit board comprises a first electrode and a second electrode separated from each other, said at least one electrode of the protective film comprises a third electrode and a fourth electrode separated from each other, the capacitive sensor comprises a first capacitive sensor formed by the first electrode together with the third electrode, and a second capacitive sensor formed by the second electrode together with the fourth electrode.

6. The medical device with electrical sensing function as described in claim 5, wherein the first capacitive sensor and the second capacitive sensor have different capacitance values.

7. The medical device with electrical sensing function as described in claim 4, wherein the protective film further comprises an insulating strip covering said at least one electrode of the protective film.

8. The medical device with electrical sensing function as described in claim 4, wherein another capacitive sensor is formed by the at least one electrode of the printed circuit board cooperating with external dielectric after removal of the protective film.

9. The medical device with electrical sensing function as described in claim 4, wherein the contact pad is disposed on the ground layer.

10. The medical device with electrical sensing function as described in claim 9, wherein the contact pad comprises a first pad, a second pad and a third pad aligned in a row, said at least one electrode of the printed circuit board comprises two electrodes, the second pad and the third pad are electrically connected with the corresponding two electrodes of the printed circuit board by two conductive traces, respectively.

11. The medical device with electrical sensing function as described in claim 1, wherein said at least one electrode of the protective film is a printed electrode made by a conductive ink printing process.

* * * * *